United States Patent [19]
Ayers

[11] Patent Number: 4,908,114
[45] Date of Patent: Mar. 13, 1990

[54] MOBILE ATOM INSERTION REACTION, MOBILE ATOM TRANSMISSIVE MEMBRANE FOR CARRYING OUT THE REACTION, AND REACTOR INCORPORATING THE MOBILE ATOM TRANSMISSIVE MEMBRANE

[76] Inventor: William Ayers, P.O. Box 5357, Princeton, N.J. 08876

[21] Appl. No.: 117,298

[22] Filed: Nov. 6, 1987

Related U.S. Application Data

[62] Division of Ser. No. 780,870, Sep. 27, 1985, abandoned.

[51] Int. Cl.⁴ .................. C25B 13/00; C25B 9/00; C25B 11/00
[52] U.S. Cl. .................. 204/252; 204/253; 204/254; 204/267; 204/268; 204/295
[58] Field of Search .................. 204/295–296, 204/252, 253–254, 73 R, 74–77, 267–268; 429/17, 19, 21, 41

[56] References Cited

U.S. PATENT DOCUMENTS

| | | | |
|---|---|---|---|
| 3,280,014 | 10/1966 | Kordesch | 204/78 |
| 3,544,375 | 12/1970 | Ruben | 429/21 |
| 4,128,701 | 12/1978 | Maricle | 429/21 |
| 4,165,271 | 8/1979 | Kadija | 204/295 |
| 4,240,882 | 12/1980 | Ang | 204/72 |
| 364,274,938 | 6/1981 | Schulten | 204/295 |
| 4,547,273 | 10/1985 | Ayers | 204/73 R |
| 4,609,451 | 9/1986 | Sammells | 204/295 |

FOREIGN PATENT DOCUMENTS

666815  7/1953  Canada .................. 204/295

Primary Examiner—John F. Niebling
Assistant Examiner—Ben C. Hsing
Attorney, Agent, or Firm—Kenneth P. Glynn

[57] ABSTRACT

Disclosed is a method of carrying out a mobile atom insertion reaction, such as a hydrogen insertion reaction, for the synthesis of reduced, hydrogenated compounds. Such reactions include the production of ammonia and hydrazine from nitrogen, formic acid and methanol from carbon dioxide, and hydrogen peroxide from oxygen. The insertion reactions are carried out at a bipolar mobile atom transmissive membrane comprising a membrane formed of a mobile atom pump material, as a hydrogen pump material, conductive atom transmissive means on one surface of the membrane and conductive atom transmissive means on the opposite surface of the membrane. The mobile atom, such as hydrogen, diffuses across the membrane, to provide a source of hydrogen on the insertion reaction side of the membrane. The insertion reaction side of the membrane is positively biased with respect to a counterelectrode so that a reactant molecule, such as carbon dioxide, is electrosorbed on that surface of the membrane. The electrosorbed reactant molecular chemically reacts with the surface hydrogen by the insertion reaction to form a reduced, hydrogenated product such as formic acid. Also disclosed is a chemical reactor, containing the membrane, and several electrical field assisted chemical reactions utilizing the membrane and reactor.

49 Claims, 5 Drawing Sheets

MOBILE ATOM INSERTION REACTION, MOBILE ATOM TRANSMISSIVE MEMBRANE FOR CARRYING OUT THE REACTION, AND REACTOR INCORPORATING THE MOBILE ATOM TRANSMISSIVE MEMBRANE

This is a division of application Ser. No. 06/780,870, filed 9/27/85, abandoned.

BACKGROUND OF THE INVENTION

Industrially important chemical processes include ammonia synthesis from nitrogen and hydrogen, hydrogen peroxide synthesis from oxygen and hydrogen, and hydrocarbon synthesis from carbon monoxide or carbon dioxide and hydrogen. All of these reactions are energy intensive.

Ammonia is industrially synthesized from the elements hydrogen and nitrogen by the Haber process in which nitrogen and hydrogen are exothermically reacted over an iron catalyst at elevated pressures, e.g. from about 100 to about 1000 atmospheres and generally from about 200 to about 300 atmospheres, and at elevated temperatures, e.g. from about 400° to about 550° centigrade and generally from about 450° to 500° degrees centigrade. The iron catalyst contains reduced oxides of iron that are doubly promoted, that is promoted with an oxide such as alumina, silica, or zirconia, and an oxide of an alkali metal or alkaline earth metal as potassium oxide or calcium oxide.

The compression of nitrogen and hydrogen gases are energy intensive processes. Moreover, the high temperatures required for the reaction provide only limited opportunities to recapture the energy of compression in other processes in an industrial chemical process.

Conventional industrial processes for the production of hydrogen peroxide use either the cyclic oxidation and reduction of hydroquinone to produce anthraquinone and hydrogen peroxide, or the direct electrochemical reduction of oxygen to hydrogen peroxide at a cathode.

In coal gasification processes, carbon monoxide and carbon dioxide are the initial intermediates, obtained by the heating of coal in the presence of steam and air under carefully controlled conditions. High temperature and high pressure catalyzed reactions, e.g., the Fisher-Tropsch reaction, of carbon dioxide or carbon monoxide with hydrogen produce a variety of hydrocarbon products, e.g. alkanes, alkenes, and other products.

Various methods of direct and indirect electrochemical reactions have also been studied to convert carbon dioxide to hydrocarbon products while avoiding high temperatures and pressures of the conventional catalytic processes.

The direct electrochemical reduction of carbon dioxide has been studied by S. Kopusta, and N. Hackerman, in Journal of the Electrochemical Society, Volume 130, pages 607 to 613 (1983). As there described, carbon dioxide is reduced and then reacts with a proton donor to produce formate. The current efficiency is high, generally about 95%, but the exchange current density is extremely low, generally about $5 \times 10^{-11}$ Amperes/cm2. This shows that the rate of reaction is low. Furthermore, the efficiency of reaction decreases as the total current through the cell increases. As the reaction of carbon dioxide must compete with the reduction of protons, electrode materials with high hydrogen overpotentials, e.g. mercury, tin, indium, or titanium dioxide must be used.

Indirect cathodic reduction of carbon dioxide has been studied by B. Fisher and R. Eisenberg, in the Journal of the American Chemical Society, Volume 102, Pages 63 to 7363 (1980) by I. S. Kolmitikov, et al, in Izu. Akad, Nauk S. S. R. Ser. Khim., Volume 1970, Page 26–50 and Volume 1972, Page 22–29, and by G. O. Evans, and C. J. Wewell in Inorganic Chim Acta., Volume 31, Pages L387–L390 (1978). The indirect reduction has been accomplished with cobalt and nickel tetraazamacrocycles, transition metal phosphine complexes, anion carbonyl hydrides and dinuclear carbonyls. The overvoltage for reduction of the complexes is less than that required for direct cathodic reduction of carbon dioxide. However, the stability of the complexes is not adequate for repeated oxidation and reduction cycles.

The reason that the indirect electrochemical reduction occurs at lower overvoltages may be that the carbon dioxide bonds are distorted by bonding to metal complexes. Carbon dioxide acts as a Lewis base with the lowest electron density being at the central carbon. Complexes with electron rich metal atoms thus bind the carbon atom.

Each of the above reactions for the synthesis of ammonia, hydrogen peroxide, and hydrocarbons involve hydrogenation of nitrogen, oxygen and carbon monoxide or carbon dioxide, respectively.

Electrochemical reduction and hydrogenation of these compounds at a cathode is inherently difficult because electrostatic repulsion between the reactant and the negatively charged cathode hinders adsorption of the reactant on the electrode and thereby limits the rate of reaction.

SUMMARY OF THE INVENTION

According to the invention described herein, the above reactions, among others, may be carried out by absorbing and passing a mobile reactant atom, e.g., atomic hydrogen through an atom transmissive, but molecule blocking membrane, e.g. a palladium membrane, to the opposite surface of the membrane, where the transmitted atom reacts with a sorbed reactant molecule to form a product. The reactant molecule is sorbed, i.e. adsorbed or electrosorbed, onto the membrane surface. Electrosorption is the electric field enhanced adsorption of a reactant at a surface. The electric field on the insertion reaction side of the membrane assists in the strong adsorption of the reactant molecule on the membrane surface and the weakening of the intramolecular bonding of the reactant molecule by the electrostatic interaction of the electric field with the electronic structure of the reactant molecule.

Hence, the reaction between the transmitted atom, e.g. hydrogen and the reactant molecule generally occurs under the influence of an electrical potential gradient or electric field between the membrane and the reactant. This electrical field controls the sorption of the reactant on the membrane and the intramolecular bond strength within the reactant thereby facilitating the reaction.

The hydrogen insertion reaction is a chemical reaction and not an electrochemical reaction. The function of the electric field on the hydrogen insertion side of the membrane is to electrosorb the reactant and distort the electronic structure of the reactant. However, the electric field does not produce an electrochemical reaction, e.g. oxidation of the electrosorbed reactant. Hence, the hydrogen insertion reaction may be called an electric field assisted chemical reaction.

The above reactions may advantageously be carried out at a hydrogen atom transmissive membrane under process conditions which strongly electrosorb the reactant (e.g. nitrogen, oxygen, or carbon monoxide) on a positively biased surface of the membrane with respect to a reference or counter electrode. This allows the reactant to chemically combine with and be reduced by a chemical insertion reaction with the transmitted hydrogen, i.e. the atomic hydrogen or a surface hydride, thereby forming the desired chemical product. The product of the insertion reaction is ammonia and/or hydrazine if nitrogen is the reactant, hydrogen peroxide if oxygen is the reactant, formate, formaldehyde, methanol, methane, or other hydrocarbons if the reactant is carbon dioxide and formaldehyde, methanol, methane or other hydrocarbons if the reactant is carbon monoxide.

The electrosorbing field can be controlled by changing the applied bias, between the membrane reaction surface and a counter electrode, or by changing the dielectric constant of the fluid and conductivity of the fluid in contact with the membrane.

The potential at the insertion reaction surface, e.g., the hydrogen insertion reaction surface can be controlled by applying a bias voltage between the membrane and a counter electrode, and by the pH of the fluid in contact with the insertion surface of the membrane.

The surface hydrogen concentration at the insertion reaction surface can be controlled by the flux of hydrogen atoms through the membrane. The flux is controlled by the concentration of atomic hydrogen on opposite sides of the membrane.

The atomic hydrogen absorbed by the membrane may be produced at the membrane surface. For example, gaseous molecular hydrogen may be decomposed on the surface of the membrane by a suitable catalyst. Alternatively, water may be electrolytically decomposed to hydrogen in at the membrane surface.

When atomic hydrogen is absorbed by the membrane, e.g. by the reduction of protons in an acid solution on one side (the hydrogen receiving side) of the membrane, some of the hydrogen diffuses into the membrane. Normally the hydrogen that diffuses to the opposite side (hydrogen donating side) of the membrane is oxidized to protons if that side of the membrane is maintained at a sufficiently positive potential with respect to a counter electrode to oxidize the surface hydrogen or hydride. However, if the anodic potential is controlled at a specific value as herein contemplated, proton evolution is substantially avoided and the transmitted hydrogen, e.g., surface hydride hydrogen or surface atomic hydrogen, attacks the electrosorbed reactant to form the reduced product by the hydrogen insertion reaction.

In the case of forming hydrocarbons, the invention resides in electrosorbing the carbon dioxide and/or carbon monoxide onto a positively biased, hydrogen donating surface of the hydrogen transmissive membrane in the configuration that most reduces the electron density at the carbon atom so that atomic hydrogen can attack the carbon-oxygen bond to form a carbon-hydrogen bond. The electrosorption of the oxygen atoms of the carbon dioxide on the positively biased side of a hydrogen transmissive membrane provides conditions for the rapid formation of e.g. formate by a hydrogen insertion at the carbon atom.

The carbon dioxide and/or carbon monoxide is bubbled into a fluid, e.g., electrolyte on the hydrogen donating side of the membrane that is positively bias with respect to a counter electrode and the potential of the surface is controlled to more strongly sorb, i.e., adsorb or electrosorb, the carbon dioxide and/or carbon monoxide. As described above, the hydrogen atoms transmitted through the membrane, e.g., as hydride or atomic hydrogen, undergo a surface reaction with the adsorbed carbon compound by attack on the electropositive carbon atom to form products such as formate, formaldehyde, methanol and methane.

Alternatively, according to a further embodiment of the invention, nitrogen may be sorbed, i.e., adsorbed or electrosorbed, onto the positively biased hydrogen donating surface of the membrane. The nitrogen may be bubbled into the fluid or electrolyte on the insertion reaction side of the membrane with the potential controlled to strongly electrosorb nitrogen onto the positively biased surface of the hydrogen transmissive membrane. As described above, the hydrogen atoms on the positively biased surface undergo the insertion reaction with the adsorbed nitrogen by attack on the nitrogen molecule thereby forming ammonia and/or hydrazine.

In this way, the high pressure and high temperatures of industrial ammonia and hydrocarbon synthesis processes are avoided.

In a further embodiment of the invention, oxygen may be sorbed, i.e., adsorbed or electrosorbed, onto the unbiased or positively biased (with respect to a counter electrode) hydrogen donating side of the membrane. Again, as described above, the hydrogen atoms on the donating side of the membrane surface undergo the insertion reaction with the adsorbed or electrosorbed oxygen by attack on the oxygen molecule. In this way a more efficient method of producing hydrogen peroxide is provided.

Accordingly, there is herein contemplated a method of inserting hydrogen into, e.g., carbon-oxygen, nitrogen-nitrogen, and oxygen-oxygen bonds by transmitting hydrogen atoms through a membrane, sorbing (as adsorbing or electrosorbing) the reactant onto the hydrogen donating surface of the membrane, and, in the case of an electrosorbed reactant, controlling the field between the membrane and reactant to control the degree of electrosorbtion of said reactant and the intro-molecular bond strength thereof. The method involves forming and absorbing the hydrogen atoms on one side (receiving side) of a transmissive membrane formed, e.g., an atomic hydrogen transmitting material. The hydrogen so absorbed passes through the membrane to the other side (donating side) of the membrane whereby to provide surface hydrogen on said donating side. Simultaneously, a reactant is sorbed, i.e. adsorbed or electrosorbed, onto said donating side of the membrane. When the hydrogen is electrolytically formed, the receiving side of the membrane is maintained at a potential, normally cathodic, high enough to evolve hydrogen, while the donating side is held at a potential, normally anodic, that facilitates the synthesis of products by electrosorption of the reactant and by facilitating the insertion reaction while minimizing the oxidation of product.

Thus, here is contemplated herein a method of electrochemically forming nitrogen compounds chosen from the group consisting of ammonia, hydrazine, and mixtures thereof by absorbing hydrogen onto the receiving side of the hydrogen transmissive membrane formed, e.g., of a hydride forming material, or of a high atomic hydrogen diffusivity material, and passing the atomic hydrogen so adsorbed through the membrane to the donating side of the membrane so as to provide hydride sites on the donating side. Simultaneously, nitrogen is sorbed, i.e., adsorbed or electrosorbed, onto the donating side of the membrane in the presence of a suitable catalyst, and the membrane is maintained at a positive potential with respect to a counter electrode high enough to evolve the desired product while substantially avoiding oxidation of the products. There is in this way the evolution or nitrogen compounds chosen from the group consisting of ammonia, hydrazine and mixtures thereof at the anodic side of the membrane. Similarly, —$NO_2$ compounds, as nitrobenzene, can be converted to —$NH_2$ compounds, as aniline, by the hydrogen insertion methods herein contemplated.

Thus, further contemplated herein is a method of forming hydrogen peroxide by the method comprising the formation and absorption of hydrogen on the receiving side of the hydrogen transmissive membrane formed of a hydride forming material or a high atomic hydrogen diffusivity material and passing the hydrogen so absorbed through the membrane to the opposite, hydrogen donating side of the membrane so as to provide hydrogen sites on the donating side. Simultaneously, oxygen is sorbed, i.e., adsorbed or electrosorbed, onto the donating side of the membrane in the presence of a suitable catalyst, or the membrane material itself. The membrane is maintained at a floating potential or a positive potential with respect to a counter electrode sufficient to facilitate the formation of the desired product while substantially avoiding oxidation or other destruction of no bias the product. There is in this way hydrogen peroxide, peroxide ion, or mixtures thereof are produced at the donating side of the membrane.

Further contemplated herein is a method of forming organic compounds as alcohols, aldehydes, ketones, acids, and alkanes by the method comprising adsorbing hydrogen on the receiving side of a hydrogen transmissive membrane formed of a hydride forming material and passing the hydrogen adsorbed thereby through the membrane to the donating side of the membrane whereby to provide hydride sites on the donating side. A reactant chosen from the group consisting of carbon monoxide, carbon dioxide and mixtures thereof is sorbed, e.g., adsorbed or electrosorbed, on the donating side of the membrane. The membrane is maintained at a positive potential to facilitate the reaction while substantially avoiding oxidation of the products. In this way, oxygen containing carbon compounds and alkanes are evolved.

This method of chemically inserting hydrogen atoms into a reactant molecule adsorbed or electrosorbed on the hydrogen donating side of the membrane can be applied to a variety of chemical and electrochemical reactions that involve hydrogenation of a reactant. For example:

(1) the formation of sorbitol from glucose $C_6H_{12}O_6 + 2H = C_6H_{14}O_6$ (2) the formation of aniline from nitrobenzene $C_6H_5NO_2 + 6H = C_6H_5NH_2 + 2H_2O$ (3) the formation of adiponitrile from acrylonitrile $2C_3H_3N + 2H = C_6H_8N_2$ In general, any chemical hydrogenation reaction, such as those described above, and any electrochemical reaction of the form:

$A + H^+ + e^- = AH$ could be accomplished in the hydrogen transmissive membrane reactor.

The hydrogen insertion membrane process has the advantage that the reactant can be strongly electrosorbed at the positively biased, hydrogen donating side of the membrane. In electrochemical reductions involving a proton at a cathode, the reactant can and often is electrostatically repulsed from the negatively charged electrode surface. The hydrogen insertion membrane process has the additional advantage that the concentration of surface atomic hydrogen on the donating side of the membrane, electric potential at the membrane surface and electric field adjacent the surface and be independently controlled.

According to a still further exemplification of the invention, a mobile atom, e.g., a hydrogen atom can be removed from a molecule. Thus, a hydrogen containing compound is brought into contact with the surface of a hydrogen or hydride depleted membrane surface, with or without an additional decomposition or dissociation catalyst to remove hydrogen. The hydrogen atoms pass through the hydrogen atom permeable membrane to an opposite side of the membrane where the atomic hydrogen may be oxidized to protons or alternatively, the hydrogen may be inserted into an acceptor molecule, such as oxygen. A negative potential with respect to a counter electrode can be maintained on the hydrogen removal side of the membrane at a level to maintain and enhance electrosorption and the hydrogen removal reaction from a polarizable or positively charged reactant.

In this way a reactant molecule may undergo a dehydrogenation reaction to form a product. For example, ethylbenzene may be adsorbed or electrosorbed on the hydrogen receiving side of the membrane and undergo the dehydrogenation reaction to form styrene. Likewise an alkane or alkene reactants may be electrosorbed on the hydrogen receiving side of the membrane and undergo the dehydrogenation reaction to form an alkene or alkyne products respectively.

The principle of chemically inserting or removing an atom from a reactant by adsorbing or electrosorbtion at a mobile atom transmissive membrane can be extended from the case of atomic hydrogen, as the mobile atom, to the case of the fast atom diffusing Group IA metal atoms as Li, Na, K, Rb, and Cs. These Group IA metal atoms are known to diffuse through membrane materials such as silicon and silicon compounds and alloys, e.g. $Li_2Si$, aluminum compounds and alloys, e.g. LiAl, or $LiC_6$ at or above room temperature.

Accordingly, there is herein further contemplated a method of chemically inserting a mobile atom from the Group IA metal atoms into a reactant molecule adsorbed or electrosorbed on the mobile atom donating surface of a Group IA atom transmissive membrane, e.g., silicon alloy $Li_2Si$.

Thus, contemplated herein is a method of forming organo-lithium compounds by adsorbing or electrosorbing a chlorinated alkane, e.g., n-butyl chloride on the lithium donating side of a lithium atom transmissive membrane, e.g. silicon alloy $Li_2Si$. The lithium atoms absorbed on the receiving side of the membrane are transmitted through the membrane to the lithium donating side of the membrane where they undergo a reaction with the adsorbed or electrosorbed reactant to form a lithiated product, e.g. n-butyl lithium.

Further contemplated herein is a method of providing sodium atoms on the donating side of a sodium atom transmissive membrane whereby a symmetrical alkane, e.g. ethane or butane and sodium bromide are produced by adsorbing or electrosorbing methyl bromide or ethylbromide, respectively, on the sodium atom donating side of the membrane.

In traditional organic chemistry, the formation of symmetrical alkanes from alkylbromides over sodium metal is called the Wurtz reaction. In the method contemplated above, better control over the reaction rate and more economical use of sodium is achieved by reacting the adsorbed or electrosorbed alkylbromide reactant at the sodium donating side of the membrane.

The bipolar membrane is useful in a chemical reactor for carrying out the hydrogen insertion methods of this invention. The reactor is characterized by a compartment containing the reactant fluid, counterelectrode, and electrical biasing supply, a second compartment containing hydrogen gas or hydrogen precursor and the bipolar membrane therebetween. The bipolar membrane is formed of a hydrogen pump material, a conductive, atom transmissive means on one side of the membrane, and conductive, atom transmissive means on the opposite side of the membrane.

THE FIGURES

The invention is particularly illustrated for the case of the hydrogen insertion reaction in the accompanying figures.

DETAILED DESCRIPTION OF THE INVENTION

Figure 1:
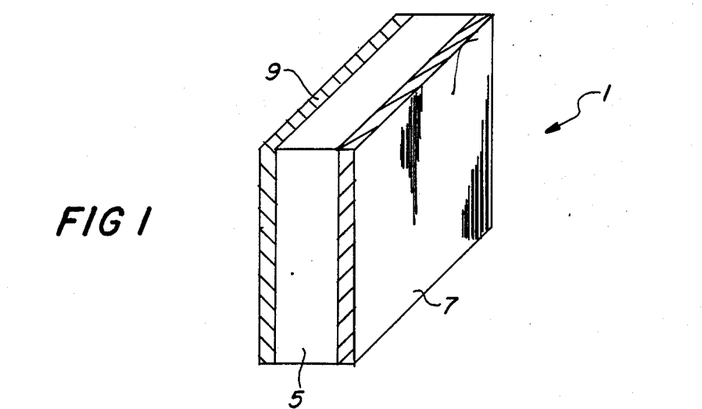
FIG. 1 shows the bipolar membrane of this invention having the hydrogen transmissive membrane with electrically conductive, mobile atom transmissive means on one surface thereof and conductive, atom transmissive means on the opposite surface thereof. Either or both the surface can have additional suitable catalyst means on either surface.

A bipolar atom transmissive membrane for the mobile atom insertion or removal reactions, e.g. hydrogen atom insertion, hydrogen atom removal, Group IA atom insertion, Group IA removal reactions is shown in FIG. 1. The bipolar membrane is useful in a chemical reactor, such as that shown in FIGS. 2, and 3 and schematically in FIGS. 4A through 4D, 5A through 5D, and 6A through 6D. The bipolar membrane 1 includes a mobile atom, e.g. atomic hydrogen permeable, molecular hydrogen impermeable membrane 5 of an atom pump material, i.e., a hydrogen pump material, electrically conductive, mobile atom transmissive biasing means 7 on one surface of the membrane 5 and electrically conductive, mobile atom transmissive biasing means 9 on the opposite surface of the membrane 5. In one embodiment, the membrane material itself is also the conductive biasing means on both or either surface.

In the case of atomic hydrogen as the mobile atom, the membrane 5 allows and enhances the flow of atomic hydrogen therethrough, for example, by hydride formation, or by diffusion or percolation of atomic hydrogen. More particularly, the membrane is characterized by the high hydrogen concentration, i.e. high hydrogen molecule, hydrogen atom, or hydride concentration, on the receiving side and lower hydrogen concentration, i.e. hydrogen molecule, hydrogen atom, hydride, or hydrogen compound concentration on the donating side, whereby to have a concentration driving force for atomic hydrogen diffusion across the membrane.

The membrane 5 is formed of a hydrogen pump material. By hydrogen pump material is meant a material that may be a low temperature hydride having an hydrogen equilibrium pressure of at least 1 standard atmospheres at a temperature of 25° centigrade, or a hydrogen content of at least $10^{22}$ hydrogen atoms per cubic centimeter at a temperature of 25° centigrade, or a hydride having a heat of formation less negative than minus 15 kilocalories per mole at 25° centigrade, or a non-hydride that is an atomic hydrogen transmissive material. Typically, the hydrogen pump material is palladium, titanium, nickel and alloys of these materials, such as $Ni_3Ti$. The transmissivity of atomic hydrogen through the hydrogen pump material is a function of hydrogen solubility in the material, hydrogen diffusivity through the material, the thickness of the material, and the interaction thereof resulting in a material of high atomic hydrogen flux. Preferably the thickness, atomic hydrogen solubility, and hydrogen diffusivity result in an atomic hydrogen flux of at least about $10^{-9}$ moles/square centimeter-second.

The electrically conductive hydrogen transmissive biasing surface, 7, may be bonded to, in contact with, or removably in contact with the membrane 5. Electrosorbed reactant and hydrogen, as hydride or atomic hydrogen, occupy sites in proximity to each other on the usually positively biased, hydrogen donating side of the membrane 5 at which the hydrogen insertion reaction occurs.

The insertion reaction surface 7 may also comprise a catalyst for the dissociation of a reactant (such as molecular nitrogen to atomic nitrogen) whereby to facilitate the formation of a product, e.g. ammonia. Most commonly, the dissociation catalyst is chosen from the group consisting of molybdenum, tungsten, iron, chromium, tantalum, nickel, and alloys, compounds and mixtures thereof.

The insertion reaction surface can further comprise an atomic hydrogen insertion catalyst. By a hydrogen insertion catalyst is meant a catalyst for the insertion of hydrogen into the intramolecular bonds of the reactant, e.g., a carbon-oxygen bond to form the oxygen containing organic materials described above, or a nitrogen triple bond to form ammonia or hydrazine or mixtures thereof. The hydrogen insertion catalyst is chosen from the group consisting of cobalt, ruthenium, osmium, nickel, palladium, platinum, and alloys, compounds and mixtures thereof.

In a particularly preferred exemplification, the insertion reaction surface comprises a material that is catalytic for both dissociation of the reactant, for example, nitrogen, and catalytic for the insertion of hydrogen into the reactant intramolecular bond, e.g., nitrogen triple bond, carbon oxygen bond, or the oxygen-oxygen bond, among others.

When the method of hydrogen transport includes hydride formation, the insertion reaction catalyst favors the hydrogen insertion reaction over the hydrogen ion formation reaction, that is, the oxidation reaction of the surface hydride. The insertion reaction catalyst should not be catalytic for oxidation of the product. Particularly desirable catalyst compositions comprise tungsten on palladium, iron on palladium, molybdenum on palladium, molybdenum on titanium, and iron on titanium.

On the opposite of the membrane, the hydrogen receiving surface 9 may be bonded to the membrane, or removably in contact with the membrane 5.

The hydrogen receiving surface, 9, is electrically conductive, transmissive to hydrogen and may comprise hydrogen formation catalyst for the evolution of molecular hydrogen, for example, a thin film material chosen from the group consisting of, for example, nickel, platinum, palladium, gold, iron, chromium, silver, tantalum, tungsten and alloys, compounds, and mixtures thereof. Alternatively, the hydrogen formation catalyst 9 may be chosen to have a high overvoltage for the evolution of molecular hydrogen such that it facilitates the formation of atomic hydrogen on the surface. This may be achieved by the use of catalyst materials such as cadmium, lead, indium, and mixtures thereof.

When the mechanism of hydrogen transport includes hydride formation, the hydrogen receiving side 9 may also comprise an atomic hydrogen formation catalyst that is inhibiting for the evolution of molecular hydrogen, thereby enhancing formation of the hydride of the membrane 5 material at the hydrogen receiving surface thereof. Preferred are materials that are catalytic for one of the two reactions occuring at or in proximity to the hydrogen receiving surface, i.e., (1) hydrogen atom formation, and (2a) hydride formation or (2b) hydrogen atom absorption. That is, the preferred materials are catalytic for electron transfer to the proton for hydrogen formation but not inhibiting for hydride formation, or hydrogen atom absorption. Especially preferred are materials that are catalytic for both (1) the electron transfer reaction and (2) the absorption and/or hydride formation reaction, and are chosen form the group consisting of titanium, vanadium, nickel, iron, and alloys compounds, and mixtures thereof.

Figure 2:
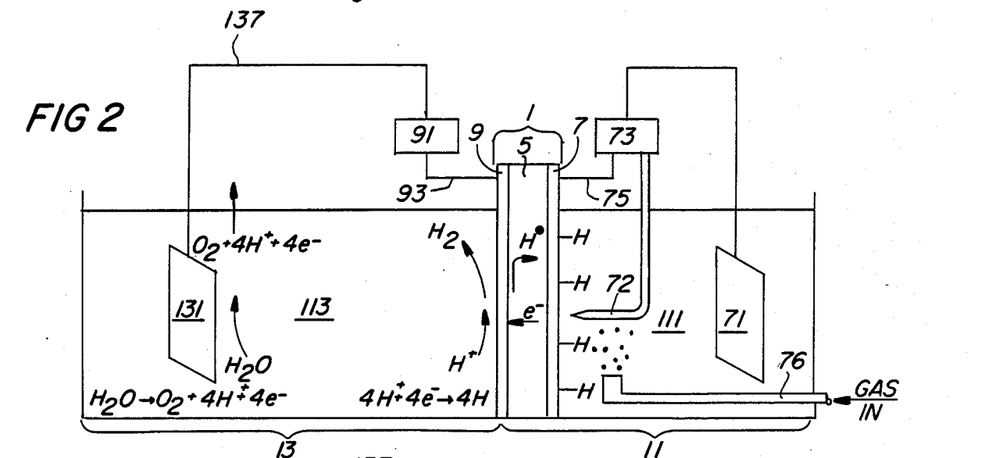
FIG. 2 shows a chemical reactor of the invention having an electrolyte compartment with a counter electrode therein, a second electrolyte compartment with a counter electrode therein, and a hydrogen transmissive membrane therebetween, with means for controlling the current to the hydrogen receiving surface and the potential at the hydrogen donating, hydrogen insertion reaction surface.
Figure 3:
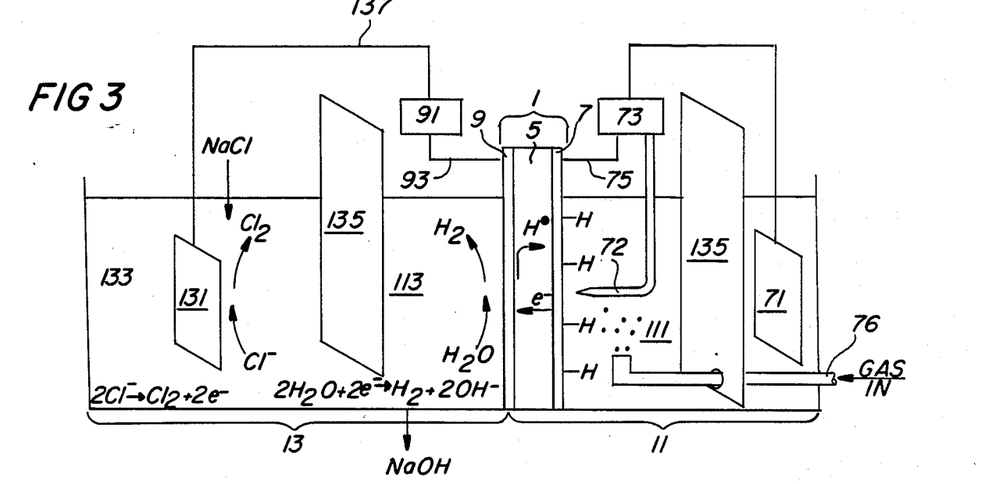
FIG. 3 shows chemical reactor for carrying out an alternative method of the invention where hydrogen is generated at the receiving surface of the membrane with chlorine rather than oxygen generated at the counter electrode on the hydrogen generating side of the membrane.
Figure 4A:
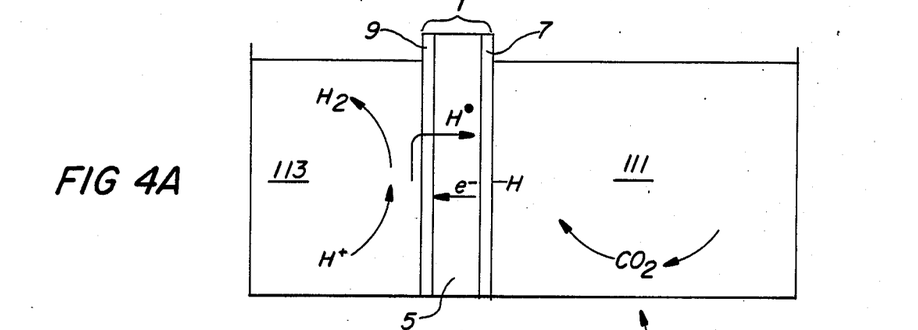
FIGS. 4A through 4D schematically show a chemical reactor with the insertion reaction of hydrogen atoms into the electrosorbed carbon oxygen bond being shown thereon to form formate.
Figure 4B:
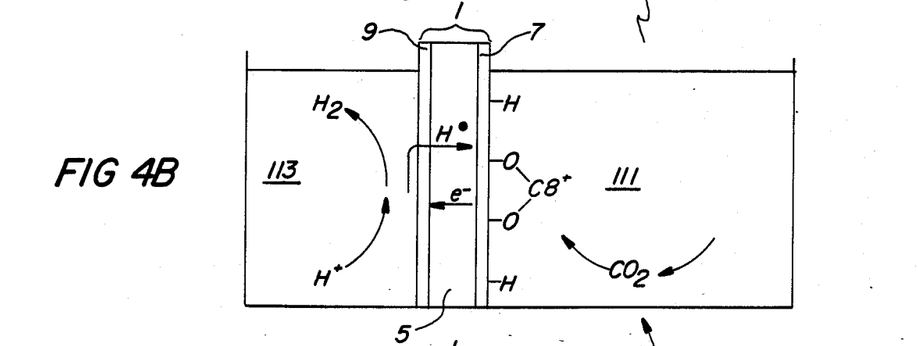
Figure 4C:
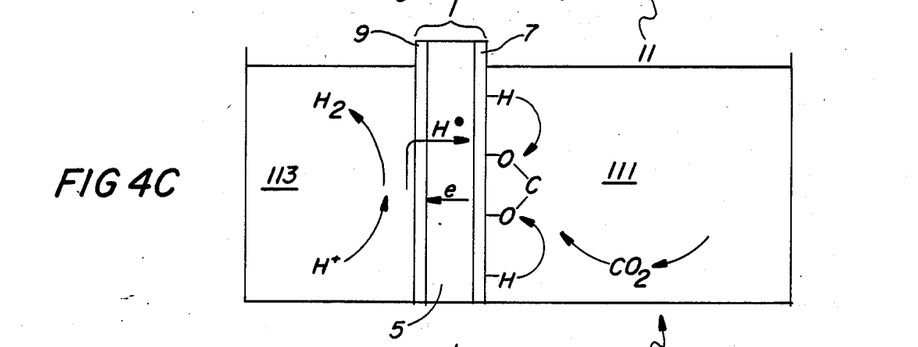
Figure 4D:
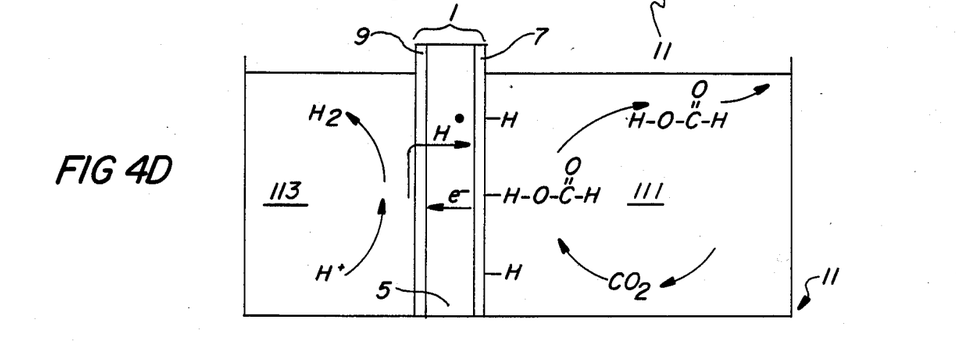
Figure 5A:
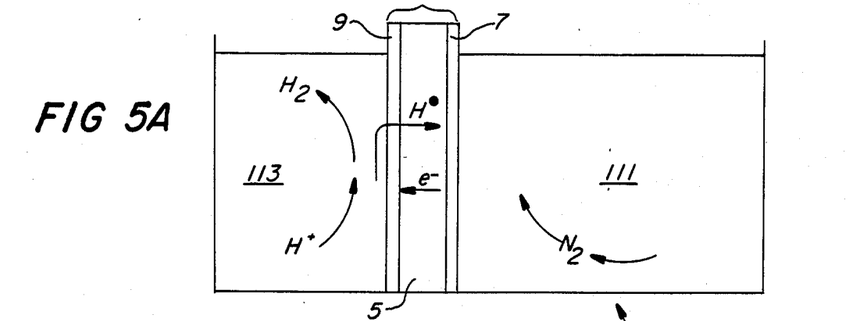
FIGS. 5A through 5D schematically show a chemical reactor of the invention with the hydrogen insertion reaction into a nitrogen molecule shown schematically at the hydrogen pump membrane to form hydrazine and ammonia.
Figure 5B:
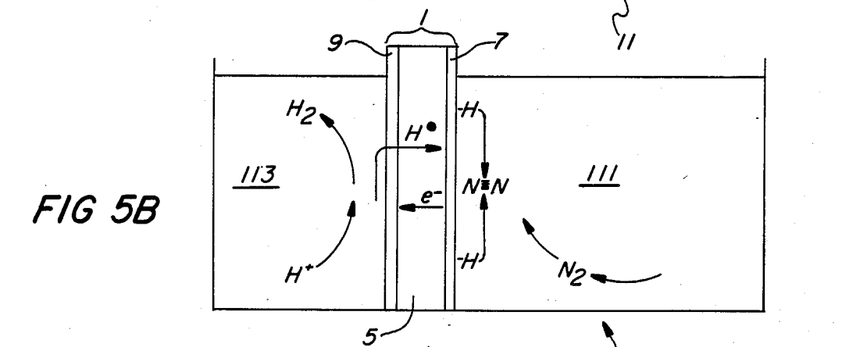
Figure 5C:
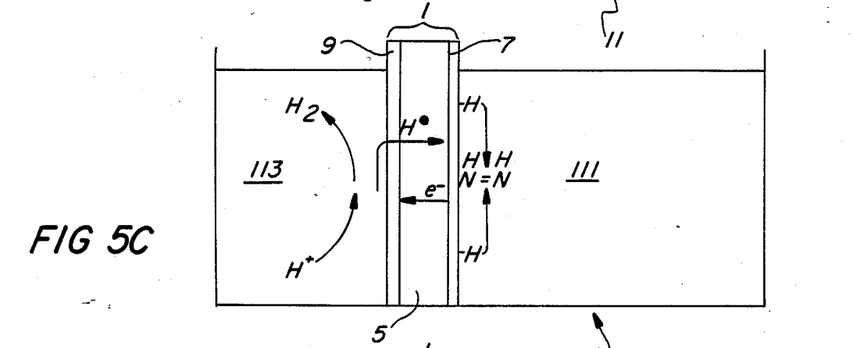
Figure 5D:
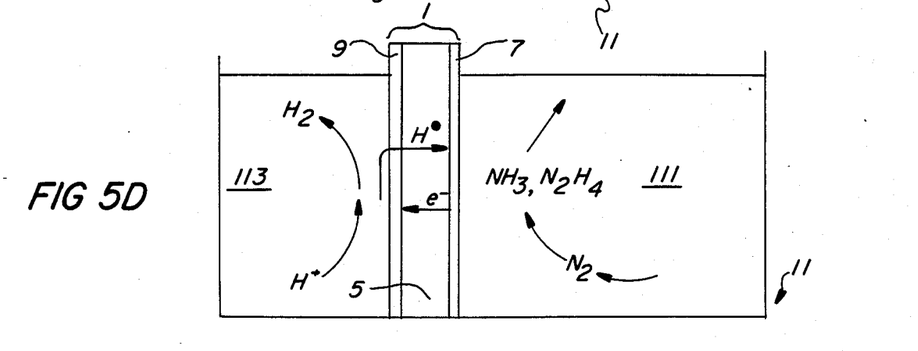
Figure 6A:
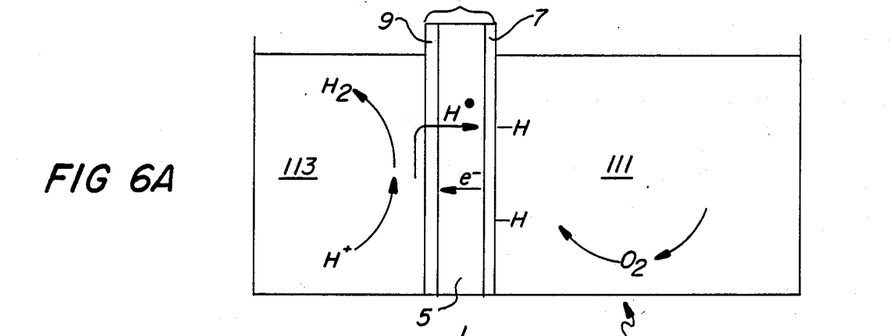
FIGS. 6A through 6D show a chemical reactor of the invention with the hydrogen insertion reaction into an oxygen molecule shown schematically thereon to form hydrogen peroxide.
Figure 6B:
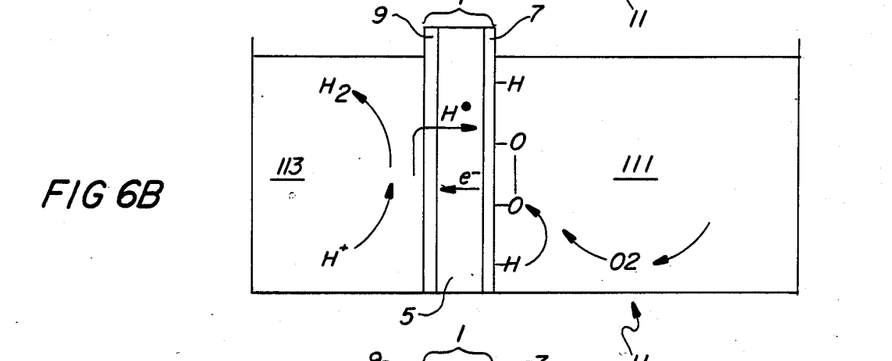
Figure 6C:
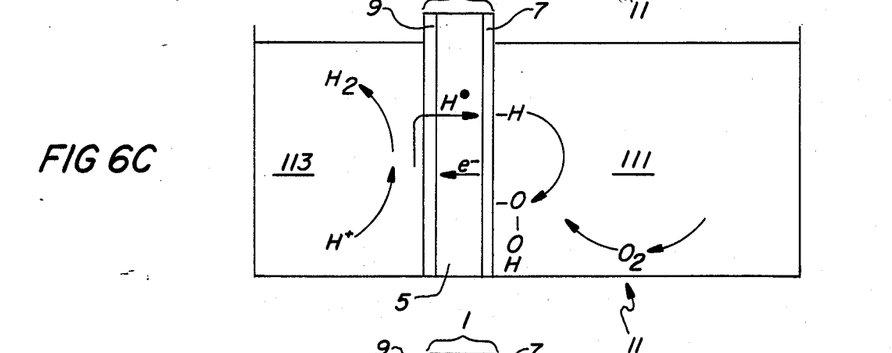
Figure 6D:
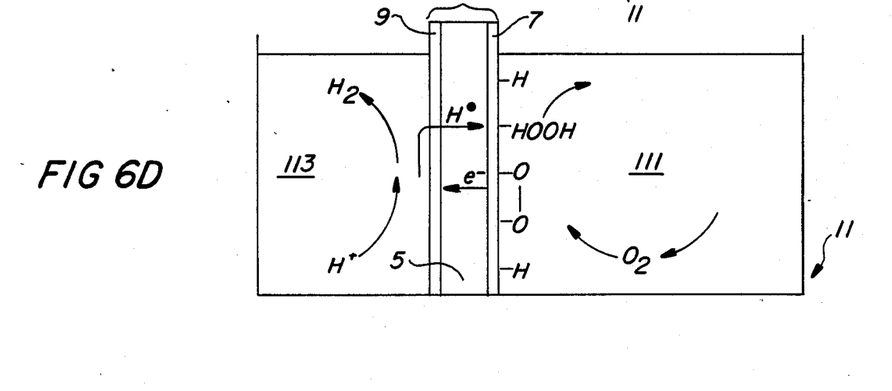

The chemical reactor of the invention is shown in particular detail in FIG. 2 and alternatively in FIG. 3 and schematically in FIGS. 4A through 4D, 5A through 5D and 6A through 6D.

The chemical reactor shown in FIG. 2 includes a hydrogen insertion reaction compartment 111, a hydrogen source compartment 113, and a bipolar membrane 1 therebetween as described above. The bipolar membrane 1 has a membrane 5 formed of a hydrogen pump material, conductive, hydrogen permeable means 7 on one side of the membrane 5 and conductive, hydrogen permeable means 9 on the opposite side of the membrane 5. The bipolar membrane 1 optionally includes mechanical support means which allow molecular or atomic transport to and from the surfaces thereof. The support may be porous. The reactor 11 further includes means for controlling the potential on the insertion reaction side, 7, of the membrane. These means are shown schematically as a voltage controller or potentiostat 73 connected to an external circuit and a reference electrode 72 and counter electrode 71 which controls the potential with respect to the reference electrode. The potential of the insertion reaction surface 7 is maintained at a high enough, usually positive, potential with respect to the reference electrode 72 to facilitate the hydrogen insertion reaction but low enough to avoid substantial oxidation of the products at the insertion reaction surface 7. The insertion reaction surface potential may be oscillated or pulsed, whereby to enhance electrosorption, reaction, or desorption.

The reactor hydrogen source side 13 includes means for controlling the current density for the electrolytic production of hydrogen on the hydrogen receiving side of the membrane. This is schematically shown as current controller 91. The current controller 91 controls current density through the cathodic current lead 93 and counter electrode 131 so as to maintain a concentration of hydrogen at the membrane and hence a flux of hydrogen through the membrane. The rate of absorption of hydrogen into the membrane is a function of the rate of hydrogen generation and hence the cathode current density.

The cathodically biased surface 9 supplies hydrogen to the membrane 5, for example by generating hydrogen by the reduction of protons or water in the electrolyte 113.

In the exemplification shown in FIG. 2, water is electrolyzed in the cell 13 whereby to generate oxygen at the anode 131 thereof and hydrogen at the hydrogen receiving surface 9. In the cell shown in FIG. 3, a permionic membrane 135 separates the electrolyte compartment 133 of the cell 13 and the electrolyte compartment 113 with chlorine being discharged at the anode 131 of the cell 13 and hydrogen being evolved at the hydrogen receiving surface 9.

The hydrogen insertion reactions are carried out by adsorbing or electrosorbing a reactant, as carbon monoxide, carbon dioxide, nitrogen or oxygen in proximity to surface hydrogen, for example, a hydride, under conditions of positive bias potential with respect to a counter electrode or no external bias. When biased the conditions are such that the reactant molecule is strongly electrosorbed so that its bonds are weaked and subject to hydrogen insertion reaction from the adjacent surface hydride, and/or transmitted hydrogen. The positive potential is sufficient to weaken or break the hydride surface bonds, but not high enough to break the bonds within the product molecule or oxidize the insertion product.

Additionally or alternatively the membrane potential may be utilized to electrosorb reactant, and optical energy, e.g., laser energy, used at a wave length to further weaken the reactant intramolecular bond strength to facilitate the hydrogen insertion reaction.

The overall insertion reaction process involves absorbing hydrogen into the hydrogen receiving surface of a hydrogen transmissive membrane, that is, a hydrogen transport material exemplified by materials having a high diffusivity for atomic hydrogen, and/or hydride forming materials, and passing the adsorbed hydrogen through the membrane 5 by diffusion to the opposite, hydrogen donating side thereof so as to provide atomic hydrogen and/or surface hydride sites on the insertion reaction side of the membrane. The transport of hydrogen may be by diffusion, or like processes. The membrane is formed of a hydrogen pump material as described above, which material absorbs hydrogen at the hydrogen receiving side and transmits the hydrogen to the opposite hydrogen insertion reaction side. Generally when hydrogen is transported by the formation of a hydride, the hydride is a low temperature hydride. By a low temperature hydride is meant a material where the hydrogen equilibrium pressure is above about 1 standard atmosphere at a temperature of about 25° degrees centigrade, or the hydrogen atom concentration is above about $10^{22}$ hydrogen atoms per cubic centimeter, or the heat of formation of the hydride is less negative than minus 15 kilocalories per mole. Exemplary low temperature hydrides from which the membrane may be formed include materials chosen from the group consisting of palladium, titanium, lanthanum, vanadium, and alloys, mixtures, and hydrides thereof. Alternatively, non-hydride forming, but atomic hydrogen soluble and/or atomic hydrogen transmissive materials may be used as the membrane material. These include silver, copper, chromium, molybdenum, iron, nickel, cobalt, platinum, and mixtures and alloys thereof. Organic and organo metallic compounds that allow atomic hydrogen to diffuse therethrough may also be used as the membrane material. The membrane 5 is a solid membrane. Only the conductive, hydrogen transmissive surfaces on the hydrogen receiving and hydrogen donating sides of the membrane need be electronic conductors. The membrane itself may be a conductor, semiconductor, or other material as long as it allows the diffusion of atomic hydrogen. The membrane is not a solid electrolyte. In this way, a controllable concentration of surface mobile atom, e.g., surface hydrogen atoms, is maintained on the insertion reaction surface of the membrane.

The reactions herein contemplated comprise adsorbing a reactant as carbon monoxide, carbon dioxide and mixtures thereof, or nitrogen, or oxygen onto the neutral or positively biased insertion reaction side of the membrane. The insertion reaction side of the membrane can have an additional catalyst such as a dissociation catalyst or a hydrogen insertion catalyst or both, as described above.

A potential is maintained on the insertion reaction side of the membrane 5 that is sufficient to facilitate the electrosorption of the reactant molecule and the hydrogen insertion reaction but low enough to avoid oxidation of the product. Hydrogen insertion products, for example, alcohols, aldehydes, ketones, or alkanes from an oxygen containing carbon compound or ammonia or hydrazine from nitrogen, or hydrogen peroxide from oxygen are formed at the insertion reaction surface. The hydrogen insertion reaction can be augmented by the absorbtion of optical energy e.g. photons from a laser, by the reactant molecule on the hydrogen insertion reaction surface.

In the case of electrolytic generation of hydrogen, the reaction carried out at the hydrogen receiving side of the membrane 9 is an electron transfer reaction where the hydrogen so formed is capable of forming mobile hydrogen, i.e., atomic hydrogen. The reaction is such that the hydrogen is produced at a sufficiently high enough rate to drive hydrogen through the membrane 5 by a concentration gradient of hydrogen across the membrane.

The electrolyte on the hydrogen receiving side typically has either an acidic pH, that is a pH less than about 7, whereby to enhance the rate of formation of atomic hydrogen, or an alkaline pH greater than 7 whereby to enhance the rate of atomic hydrogen formation by the reduction of water.

Because the hydrogen insertion reaction is a chemical reaction rather than an electrochemical reaction, the liquid on the insertion reaction side of the membrane need not be an electrolyte. It may also be an aqueous or non-aqueous liquid and that is nonconductive or a dielectric or it may be an electrolyte. However, typically the liquid is an aqueous or a nonaqueous electrolyte solution. The liquid should have a high solubility for the reactant, e.g., carbon dioxide or carbon monoxide, nitrogen, or oxygen.

The hydrogen insertion reaction is not an electron transfer reaction. The electric field at the insertion reaction surface is believed to distort and weaken the bonds of the adsorbed reactant, in the presence of and in proximity to a surface hydrogen, i.e., a weakly bonded hydride or atomic hydrogen. In this way, it is believed that the field which distorts the bonds in the absorbed reactant and, in the case of a weakly bonded hydride, weakens the metal-hydride bond, allows the hydrogen to be inserted at the distorted bond of the adsorbed reactant as shown in FIGS. 4A through 4D, 5A through 5D, and 6A through 6D. Moreover, the insertion reaction may be augmented by optical energy, as the absorption of laser light at the appropriate wave length.

The hydrogen insertion reaction, with respect to carbon dioxide involves, for example, the overall reaction $$2H + CO_2 = HCOOH$$

which includes the reaction to form and absorb hydrogen on the hydrogen receiving side of the membrane:

$$M + H^+ + e^- = M-H$$

where M is a hydrogen absorbing membrane material such as a hydride forming material. The hydrogen insertion reactions on the opposite hydrogen donating, usually positively biased side of the membrane are:

(1) $CO_2 = CO_2(ads)$ (2) $M - H + CO_2(ads) = M + HCOO(ads)$ (3) $M - H + HCOO(ads) = M + HCOOH(ads)$ (4) $\underline{HCOOH(ads) = HCOOH}$
$CO_2 + 2M - H = HCCOH + 2M$ The formic acid product may also undergo the hydrogen insertion reaction to form formaldehyde, $HCOOH + 2MH = HCOH + H_2O + 2M$ Likewise formaldehyde may react to form methanol, $HCOH + 2MH = CH_3OH + 2M$ and methanol may react to form methane
$CH_3OH + 2MH = CH_4 + H_2O + 2M$ A possible side reaction on the insertion reaction side of the membrane when positively biased is the electrochemical oxidation of the surface hydride:

$M-H = M + H^+ + e^-$

The hydrogen insertion reaction may also be utilized to insert hydrogen into an oxygen molecule according to the overall reaction:

$H_2 + O_2 = H_2O_2$ which may be broken down into the above reaction on the atomic hydrogen receiving side of the membrane, and on the insertion side of the membrane, even in the absence of an applied bias:

$O_2 = O_2(ads)$ $O_2(ads) + MH = HO_2 + M$ $\underline{HO_2 + MH = H_2O_2 + M}$
$O_2 + 2M - H = H_2O_2 + 2M$ Alternatively, the hydrogen insertion reaction may be utilized to insert hydrogen into a nitrogen molecule to form ammonia molecules according to the overall reaction:

$3H_2 + N_2 = 2NH_3$ which may be broken down into the reaction on the hydrogen receiving side:

$M + H + e = MH$ and the insertion reaction of the hydrogen donating, usually positively biased side of the membrane:

(1) $N_2 = N_2(ads)$ (2) $N_2(ads) = 2N(ads)$ (3) $N(ads) + M - H = NH(ads) + M$ (4) $NH(ads) + M - H = NH_2(ads) + M$ (5) $NH_2(1ads) + M - N = NH_3(1ads) + M$ (6) $\underline{NH_3(ads) = NH_3}$
$N_2 + 6M - H = 2NH_3 + 6M$ To produce hydrazine the reactions on the hydrogen donating usually positively biased, side are:

(1) $N_2 = N_2(ads)$ (2) $N_2(ads) + M - H = HN_2 + M$ (3) $\underline{HN_2(ads) + M - N = N_2H_2 + M}$
$N_2 + 2M - H = N_2H_2 + 2M$ Turning now to FIGS. 4A through 4D, there is shown a method of chemically forming an organic acid, as formic acid, by the hydrogen insertion reaction using the reactant carbon dioxide. Hydrogen is absorbed onto the hydrogen receiving side of the hydrogen transmissive membrane 5. The hydrogen so absorbed is passed through the membrane 5 to the opposite hydrogen donating, hydrogen insertion reaction side of the membrane 5, while carbon dioxide is adsorbed or electrosorbed onto the same side of the membrane 5. A positive potential with respect to a counter electrode is maintained high enough to electrosorb carbon dioxide or mixtures thereof but low enough to avoid oxidation of the desired product. In this way, a product, as formic acid, is evolved at the insertion reaction side of the membrane 5.

The reaction on the hydrogen receiving side of the membrane, 9, involves electron transfer to a proton to form a hydrogen atom on the surface of the membrane. The electrolyte on this side of the membrane is typically an acidic or alkaline electrolyte, for example an aqueous solution of a mineral acid, or an aqueous solution of sodium hydroxide. Hydrogen is evolved at the surface 9 at a high enough rate to maintain hydrogen flow to and hydrogen atom flow through the membrane 5. This generally requires a current density from about 1 milliampere per square centimeter to about 100 milliamperes per square centimeter.

The membrane 5 is formed of a hydrogen pump material that absorbs hydrogen on the hydrogen receiving side and donates hydrogen at the hydrogen insertion reaction side. The membrane 5 is formed of a low temperature hydride and/or a high hydrogen diffusivity material as described above. Preferably, the hydrogen pump material is palladium having a thickness of from about 5 microns to about 30 microns.

The insertion reaction surface may be the hydrogen pump material or another material is such as to enhance electrosorption and chemisorption of the carbon monoxide, carbon dioxide or mixtures thereof onto the membrane 5, and insertion of hydrogen into the adsorbed carbon monoxide or carbon dioxide. Exemplary insertion reaction materials include molybdenum, iron, and tungsten.

For example, 0.1 to 10 micro grams per square centimeter of molybdenum may be deposited on the palladium membrane 5 by any of the methods of electrodeposition, sputtering, reactive sputtering, glow discharge, or chemical vapor deposition. Likewise, the hydrogen receiving surface 9 may have a dispersion or film of 0.1 to 10 micro grams per square centimeter of e.g., platinum deposited on the opposite surface of the palladium membrane 5 by any of the methods of electrodeposition, physical vapor deposition sputtering, reactive sputtering, glow discharge deposition, or chemical vapor deposition.

The reaction may be and has been carried out in a chemical reactor having a hydrogen insertion reaction compartment 11 of about 2.5 centimeters high by 2.5 centimeters wide by 10 centimeters long of 0.5 centimeter thick plexiglass (R), and a hydrogen source compartment 13 of about 2.5 centimeters wide by about 2.5 centimeters high by about 10 centimeters long formed of 0.5 centimeter thick Plexiglass (R). The hydrogen pump bipolar membrane 1 is a membrane of 2.5 centimeters by 2.5 centimeters by 25 microns thick palladium.

The potential on the hydrogen insertion reaction side of the membrane is controlled by a reference electrode 72 and e.g., a BAS CV 27 potentiostat voltage controller 73 and counterelectrode 71 while the current on the hydrogen receiving side of the membrane is controlled by e.g., a Hewlett Packard 6200 B constant power supply 91. The cell 11 is operated with a liquid of carbon dioxide saturated 0.1M $NaHCO_3$ and an electrolyte of 0.5M $H_2SO_4$ on the hydrogen receiving side, 13, of the membrane.

The cell is operated with the insertion reaction side of the membrane at a potential of $-0.10$ to $0.50$ volts versus a silver/silver chloride reference electrode and a hydrogen receiving side current density of 15 milliamperes per square centimeter.

In this way, formic acid, formaldehyde, and methanol are each produced by the hydrogen insertion reaction into electrosorbed carbon dioxide at a rate of about $6 \times 10^{-8}$ moles per square centimeter per second.

According to an alternative exemplification of this invention, there is provided a method of forming ammonia, hydrazine and mixtures thereof by inserting the surface hydrogen into electrosorbed or adsorbed nitrogen, as shown in FIGS. 5A to 5D. As there shown, hydrogen is absorbed on the hydrogen receiving side of the hydrogen transmissive membrane 5 formed, e.g., of a hydride forming or high hydrogen diffusion material, and passing the atomic hydrogen through the membrane to the opposite hydrogen donating, hydrogen insertion reaction side of the membrane 5 while electrosorbing nitrogen onto the insertion reaction side of the membrane 5. A positive potential is maintained on the insertion reaction side of the membrane 5 with respect to a counter electrode sufficient to electrosorb nitrogen but low enough to avoid oxidation of the product. The products, for example ammonia, hydrazine or mixtures thereof are evolved from the insertion reaction side of the membrane 7.

On the hydrogen receiving side of the membrane, 9, protons are electrochemically reduced to form hydrogen. The surface 9 may be an electron transfer catalyst and/or a hydride formation catalyst. The electrolyte is an aqueous solution of mineral acid or a base, whereby to enhance hydrogen formation at the membrane.

Hydrogen is evolved at the hydrogen receiving side of membrane, 9 at a rate high enough to maintain an atomic hydrogen flow through the membrane 5; for example a hydrogen evolution current density of about 1 milliamperes per square centimeter to about 100 milliamperes per square centimeter.

The membrane 5 is a hydrogen pump material that absorbs hydrogen on the hydrogen receiving side and donates hydrogen on the hydrogen insertion reaction side, for example, a low temperature hydride as described above, or a high hydrogen diffusivity material and exemplified by palladium. Typically the palladium has a thickness of about 5 microns to about 50 micron.

The hydrogen insertion reaction surface, 7, may also have a dispersion or thin film of 0.1 to 10 micrograms per square centimeter of iron deposited on the palladium by, e.g., electrodeposition, sputtering, reactive sputtering, glow discharge, or chemical vapor deposition. Also, the hydrogen receiving surface 9 may be a film or dispersion of 0.1 to 10 micrograms per square centimeter of platinum deposited on the opposite surface of the palladium membrane 5 by electrodeposition, sputtering, reactive sputtering, glow discharge, or chemical vapor deposition.

In a particular embodiment, a chemical reactor is prepared having an insertion reaction compartment 11, 2.5 centimeters wide by 10 centimeters long by 2.5 centimeters high formed of 0.5 centimeter Plexiglass (R), and a hydrogen source compartment 13, 2.5 centimeters wide by 2.5 centimeters high by 10 centimeters long formed of 0.5 centimeter Plexiglass (R). The hydrogen pump bipolar membrane 1 is a membrane 5 of 2.5 centimeters by 2.5 centimeters by 25 micron thick palladium.

The potential on the hydrogen insertion reaction surface is controlled by a reference electrode 72 and a BAS CV 27 potentiostat controller 73 while the current density is controlled by a Hewlett Packard 6200B current controller 91.

The cell 11 is operated with an electrolyte of nitrogen saturated $H_2SO_4$ or water. The insertion reaction membrane potential is controlled at 0.00 to 0.80 volt versus a Ag/AgCl reference electrode while the current density on the hydrogen receiving side of the membrane is controlled at 10 to 15 milliamps per square centimeter. In this way, ammonia and hydrazine are each produced at a rate of at least about $2 \times 10^{-12}$ moles per square centimeter per second.

According to an alternative exemplification of this invention, there is provided a method of forming hydrogen peroxide by inserting the surface hydride into adsorbed or electrosorbed oxygen as shown in FIGS. 6A through 6D. As there shown, hydrogen is absorbed on the hydrogen receiving side of the hydrogen transmissive membrane 5, and passing the atomic hydrogen through the membrane to the insertion reaction side of the membrane 5 while adsorbing or electrosorbing oxygen onto the insertion reaction side of the membrane 5. A potential is maintained on the insertion reaction side of the membrane 5 high enough to electrosorb oxygen but low enough to avoid oxidation of the product. A product, hydrogen peroxide is produced on the insertion reaction side of the membrane 5 from the hydrogen insertion reaction.

On the hydrogen receiving side of the membrane, hydrogen is electrochemically formed by the electron transfer from the surface 9 to a proton. The surface 9 may be the membrane material or an electron transfer catalyst, for example platinum or nickel. The electrolyte is, for example, an aqueous solution of mineral acid, whereby to enhance hydrogen formation and absorption by the membrane.

Hydrogen is evolved on the hydrogen receiving side of the membrane 9 at a rate high enough to maintain an atomic hydrogen flow through the membrane 5, for example at a current density of about 10 milliamperes per square centimeter to about 500 milliamperes per square centimeter.

The membrane 5 is a hydrogen pump material that adsorbs hydrogen on the hydrogen receiving side and donates hydrogen on hydrogen insertion reaction side, for example, a low temperature hydride as described above, or a high hydrogen diffusivity material exemplified by palladium. Typically the palladium has a thickness of about 5 microns to about 30 microns.

The hydrogen insertion reaction surface, 7, may also have a dispersion or thin film of a catalyst of 0.1 to 10 micrograms per square centimeter deposited on the palladium by the method of electrodeposition, sputtering, or chemical vapor deposition.

Likewise, a film or dispersion of platinum of 0.1 to 10 micrograms per square centimeter thereof may be deposited on the opposite surface of the palladium membrane 5 by the method of electrodeposition, sputtering, reactive sputtering, glow discharge, or chemical vapor deposition.

In a particular embodiment, a chemical reactor is prepared having an anodic compartment 11, 2.5 centimeters wide by 2.5 high by 10 centimeters long formed of 0.5 cm Plexiglass (R) an a compartment 13, 2.5 centimeters wide by 2.5 centimeters high by 10 centimeters long formed of 0.5 centimeter Plexiglass (R). The hydrogen pump bipolar membrane 1 is a membrane 5 of 2.5 centimeters by 2.5 centimeters by 25 micron thick palladium.

The potential of the hydrogen insertion reaction surface is controlled by a counter electrode 71, and BAS CV27 model potentiostat controller 73 while the current density on the hydrogen receiving side is controlled by a Hewlett-Packard 6200B model current controller 91.

The cell 11 is operated with an oxygen saturated liquid of 0.5M $H_2SO_4$ or water. The hydrogen insertion reaction to form hydrogen peroxide from adsorbed oxygen is so facile that an applied bias between the insertion reaction side of the membrane and a counter electrode is not necessary to stimulate electrosorption or the reaction. However, the reactor has also been operated with the membrane potential on the hydrogen insertion reaction side at 0.00 to +0.40 volts versus a Ag/AgCl reference electrode. The current density on the hydrogen receiving side is controlled at 10 to 15 milliamps per square centimeter. In this way, hydrogen peroxide is produced at a rate of at least $10^{-8}$ moles/$cm^2$-second.

Figure 7:
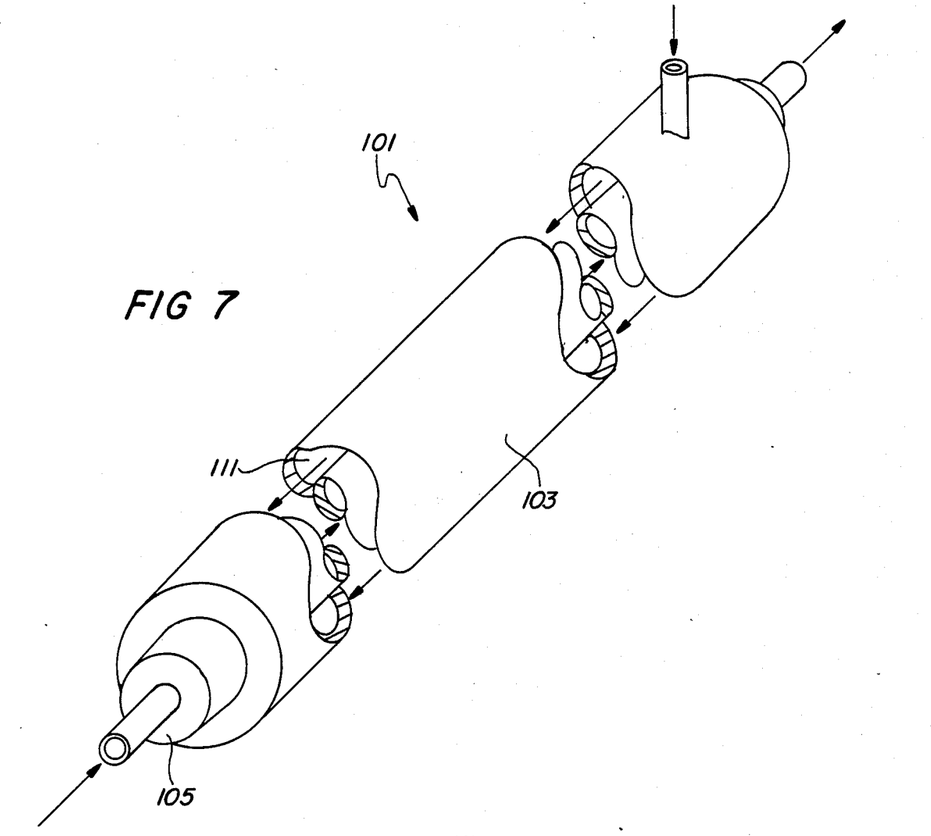
FIG. 7 shows an isometric view of a countercurrent flow tubular reactor for carrying out the hydrogen insertion reactions herein contemplated.
Figure 8:
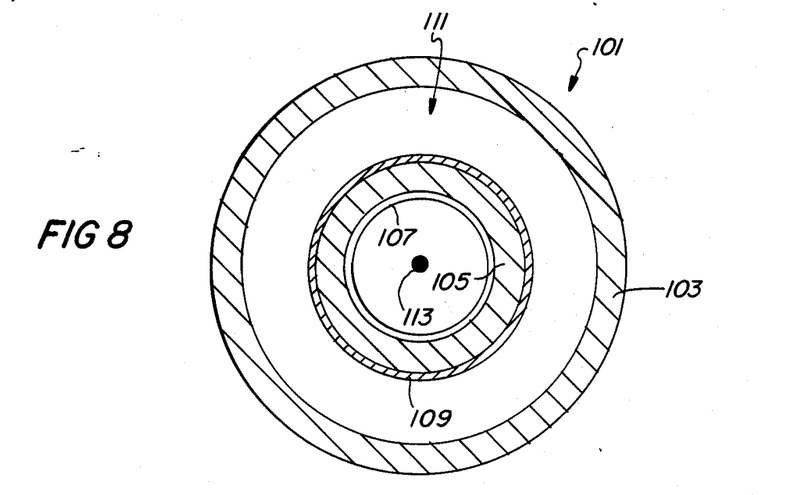
FIG. 8 shows a cross sectional view of the reactor shown in FIG. 7.

FIGS. 7 and 8 show a counter current flow tublar reactor 101 for carrying out an alternative method of this invention. As there shown, the shell side 111 fluid contains the mobile reactant, e.g., hydrogen gas, or a precursor thereof, as water. The tube side 105 fluid contains the reactant into which the mobile atom, e.g., hydrogen, is to be inserted. The reactor 101 includes an outer concentric compartment 103 and an inner, annular compartment 105.

The inner, annular compartment 105 is formed of a wall of a material that allows transmission of the mobile atom therethrough. For example, for hydrogen insertion reactions, the inner annular vessel is formed of a material that allows transmission of hydrogen therethrough. The mechanism of hydrogen transmissions can be atomic hydrogen diffusion, hydride formation, or a combination thereof.

The inner, annular compartment 105 further includes on the inner surface thereof a film, layer, coating, or surface of a catalyst 107 for the insertion reaction. The catalyst 107 is catalytic for the contemplated insertion reaction, enhancing the chemisorption or electrosorption of the reactant, or allowing electrical potential control of the electrosorption of the reactant molecule or of the intramolecular bond strength. An electrical bias between counter electrode 113 and catalyst 107 maintains potential control at the surface 107.

When the reaction is a hydrogen insertion reaction, the inner annular compartment 105 is formed of hydride forming material, or a material having a high atomic hydrogen diffusivity.

The outer surface of the inner annular compartment 105 includes a coating, film, layer, or surface 109 of a catalyst for decomposition of the precursor of the mobile atom, e.g. a water decomposition catalyst, a molecular hydrogen decomposition catalyst, a water decomposition electrocatalyst, or an atomic hydrogen formation electrocatalyst. In the case of electrolytic hydrogen generation, a constant current is applied between the catalyst 109 and counterelectrode 103 to evolve hydrogen.

While the tubular reactor has been shown in a configuration for a shell side mobile atom and a tube side reactant, it is to be understood that the reactant can be the shell side fluid and the mobile atom or precursor thereof can be the tube side reactant.

While the reactions and reaction vessels have been described with respect to water and aqueous streams as the source of hydrogen, it is to be understood that gaseous hydrogen can be the source of the mobile hydrogen atoms. When gaseous hydrogen or a hydrogen containing gas or vapor is the hydrogen atom source, the gaseous hydrogen can be decomposed by a surface catalyst 9, 109, in proximity to the hydrogen pump membrane 5, 105. As herein contemplated, hydrogen gas is brought into contact with a suitable catalyst 9, 109 on the hydrogen side of the hydrogen atom permeable membrane 5, 105, and decomposed to form hydrogen atoms. The hydrogen atoms pass through the hydrogen permeable membrane 5, 105, e.g. by forming a weakly bonded hydride, by diffusion, or by a combination thereof, to the insertion side of the membrane 5, 105. The hydrogen insertion reactant is adsorbed, e.g., chemisorbed or electrosorbed, onto a catalyst 7, 107, on the opposite side of the membrane 5, 105, under the influence of an electrical field between surface 107 and counter electrode 113. The electrical field is believed to control the adsorption and intramolecular bond strength, thereby enhancing hydrogen insertion. The insertion reaction may be further enhanced by the absorbtion of optical energy by the reactant molecule.

According to a still further exemplification of the invention, a mobile atom, e.g., a hydrogen atom or an alkali metal atom can be removed from a molecule. Thus, a hydrogen containing compound is brought into contact with a suitable decomposition or dissociation catalyst on the surface of a hydrogen or hydride depleted membrane surface, to remove hydrogen. The hydrogen atoms pass through the hydrogen atom permeable membrane to an opposite, optionally positively biased side of the membrane where the atomic hydrogen may be inserted into acceptor molecule, as oxygen or oxidized to protons. A negative potential with respect to a counter electrode may be maintained on the hydrogen removal side of the membrane at a level to maintain and enhance electrosorption and the hydrogen removal reaction from a polarizable or positively charged reactant.

While the invention has been described with respect to certain particularly preferred exemplifications and embodiments thereof, it is not intended to limit the scope of the invention thereby but only by the claims appended hereto.

I claim:

1. A bipolar atom transmissive membrane for hydrogen insertion reactions comprising:
   (a) a membrane comprising atom permeable, molecular impermeable, atom pump material, said membrane having a hydrogen insertion reaction side and a hydrogen receiving side;
   (b) electrically conductive, atom permeable, biasing means on the hydrogen insertion reaction side of said membrane to control the surface potential thereof;
   (c) electrically conductive, atom permeable biasing means on the opposite, hydrogen receiving side of said membrane;
   (d) a first power source connected to said biasing means on said hydrogen insertion reaction side; and,
   (e) a second power source connected to said biasing means on said hydrogen receiving side.

2. The membrane of claim 1 wherein said membrane is a hydrogen pump material which absorbs hydrogen on one side and desorbs hydrogen on the opposite side.

3. The membrane of claim 2 wherein said hydrogen pump material absorbs hydrogen at a negatively biased surface and desorbs hydrogen at an opposite, positively biased surface.

4. The membrane of claim 2 having an atomic hydrogen flux of at least about $10^{-9}$ moles/square centimeter-second.

5. The membrane of claim 2 wherein said hydrogen pump material is a low temperature hydride having a hydrogen equilibrium pressure of at least 1 standard atmosphere at a temperature of 25 degrees centigrade.

6. The membrane of claim 2 wherein said hydrogen pump material has a hydrogen content of at least $10^{22}$ hydrogen atoms per cubic centimeter at a temperature of 25 degrees centigrade.

7. The membrane of claim 2 wherein said hydrogen pump material forms a hydride having a heat of formation less negative than minus 15 kilocalories per mole at 25 degrees centigrade.

8. The membrane of claim 2 wherein said hydrogen pump material is chosen from the group consisting of palladium, titanium, nickel and alloys and hydrides thereof.

9. The membrane of claim 1 wherein the bipolar membrane is mechanically supported by support means allowing molecular and atomic transport to and from said sides of said membrane.

10. The membrane of claim 1 wherein said biasing means on the hydrogen insertion reaction side comprises a mobile atom transmissive, reactant dissociation catalyst.

11. The membrane of claim 1 wherein said biasing means on the hydrogen insertion reaction side of the membrane comprises a hydrogen insertion catalyst.

12. The membrane of claim 11 wherein said hydrogen insertion catalyst is chosen from the group consisting of cobalt, ruthenium, osmium, nickel, palladium, platinum, and alloys, compounds and mixtures thereof.

13. The membrane of claim 1 wherein said biasing means on the hydrogen receiving side comprises a hydrogen atom transmissive hydrogen formation catalyst.

14. The membrane of claim 13 wherein said hydrogen formation catalyst is chosen from the group consisting of platinum, palladium, gold, iron, chromium, silver, tantalum, tungsten, and alloys, compounds and mixtures thereof.

15. The membrane of claim 13 wherein said biasing means includes a catalyst that enhances formation of atomic hydrogen while substantially inhibiting evolution of molecular hydrogen.

16. The membrane of claim 15 wherein said hydrogen formation catalyst is chosen from the group consisting of cadmium, lead, indium, and mixtures thereof.

17. The membrane of claim 1 wherein said biasing means on the hydrogen receiving side comprises a hydride formation catalyst.

18. The membrane of claim 17 wherein said hydride formation catalyst is chosen from the group consisting of palladium, titanium, vanadium, nickel, lanthanum, and alloys, compounds and mixtures thereof.

19. A chemical reactor comprising:
   (a) an insertion reaction compartment;
   (b) a mobile atom generation compartment; and,
   (c) a bipolar membrane therebetween having:
      (i) a membrane formed of a mobile atom permeable, molecule impermeable atom pump material;
      (ii) conductive, a first mobile atom transmissive biasing means on one side of said membrane, facing the insertion reaction compartment so as to affect the potential on said surface and thereby affect the formation of a mobile atom insertion reaction product; and,
      (iii) a second and separate conductive mobile atom transmissive biasing means on the opposite side of the membrane, facing the mobile atom generation compartment.

20. The chemical reactor of claim 19 wherein said atom transmissive membrane absorbs the mobile atom on the mobile atom generation compartment side of said membrane and desorbs the mobile atom on the insertion reaction compartment side of the membrane.

21. The chemical reactor of claim 20 comprising means for controlling mobile atoms on the insertion reaction compartment side of the membrane.

22. The chemical reactor of claim 21 wherein said means for controlling the mobile atoms on the insertion reaction compartment side of the membrane comprises control of the mobile atom flux by a concentration gradient of mobile atoms across the membrane.

23. The chemical reactor of claim 19 comprising means for controlling the insertion reaction compartment side potential with respect to a reference or counter electrode.

24. The chemical reactor of claim 19 comprising means for controlling the pH and composition of fluid in contact with the insertion reaction compartment side of the membrane whereby to control potential of the insertion surface of the membrane with respect to a reference electrode.

25. The chemical reactor of claim 19 comprising means for controlling an electrical bias between the insertion reaction compartment side and a counter electrode whereby to control potential of the insertion reaction compartment side of the membrane.

26. The chemical reactor of claim 19 comprising means for controlling potential of the insertion reaction compartment side to facilitate the insertion reaction while substantially avoiding destruction of product.

27. The chemical reactor of claim 19 comprising means for controlling the dielectric constant and conductivity of fluid in contact with the insertion reaction compartment side of the membrane whereby to control potential at the insertion reaction compartment side of the membrane.

28. The chemical reactor of claim 19 comprising means for pulsing or oscillating potential at the insertion reaction compartment side.

29. The chemical reactor of claim 19 comprising means for controlling an electrochemical reaction to generate mobile atoms on the mobile atom generation compartment side of the membrane.

30. The chemical reactor of claim 19 comprising means for controlling an electrochemical reaction on the mobile atom generation side so as to maintain a flux of mobile atoms through the membrane.

31. The chemical reactor of claim 19 comprising means for supplying mobile atom precursors to the mobile atom generation side of the membrane.

32. The chemical reactor of claim 19 comprising means for generating atomic hydrogen at the mobile atom generation compartment side of the membrane by reduction of water, protons, hydrogen or hydrogen atom precursors.

33. The chemical reactor of claim 19 wherein the atom pump material is a hydrogen atom pump material that absorbs hydrogen at the mobile atom generation compartment side and desorbs hydrogen at the insertion reaction compartment side.

34. The chemical reactor of claim 33 having an atomic hydrogen flux of at least $10^{-9}$ moles/square centimeter second.

35. The chemical reactor of claim 33 comprising means for controlling potential of the insertion reaction compartment side to neutral or positive bias potentials to facilitate the mobile atom insertion reaction at potentials to substantially avoid oxidation of the insertion reaction product.

36. The chemical reactor of claim 33 wherein the hydrogen pump material is a low temperature hydride having a hydrogen equilibrium pressure of at least 1 standard atmosphere at a temperature of 25 degrees centigrade.

37. The chemical reactor of claim 33 wherein the hydrogen pump material has a hydrogen content of at least $10^{22}$ hydrogen atoms per cubic centimeter at a temperature of 25 degrees centigrade.

38. The chemical reactor of claim 33 wherein the hydrogen pump material forms a hydride having a heat of formation less negative than minus 15 kilocalories per mole at 25 degrees centigrade.

39. The chemical reactor of claim 33 wherein the hydrogen pump material is chosen from the group consisting of palladium, titanium, and alloys and hydrides thereof.

40. The chemical reactor of claim 19 wherein the insertion reaction compartment side of the membrane comprises a reactant dissociation catalyst.

41. The chemical reactor of claim 40 wherein the dissociation catalyst is chosen from the group consisting of molybdenum, tungsten, iron, chromium, tantalum, and alloys, compounds and mixtures thereof.

42. The chemical reactor of claim 19 wherein the insertion reaction compartment side of the membrane comprises a hydrogen insertion catalyst.

43. The chemical reactor of claim 42 wherein the hydrogen insertion catalyst is chosen from the group consisting of cobalt, ruthenium, osmium, nickel, palladium, platinum, and alloys, compounds and mixtures thereof.

44. The chemical reactor of claim 19 wherein the mobile atom generation compartment side of the membrane comprises a hydrogen formation catalyst.

45. The chemical reactor of claim 44 wherein the hydrogen formation catalyst is chosen from the group consisting of platinum, palladium, gold, iron, chromium, silver, tantalum, tungsten, and alloys, compounds, and mixtures thereof.

46. The chemical reactor of claim 19 wherein the mobile atom generating compartment side of the membrane comprises a catalyst that enhances formation of atomic hydrogen while substantially inhibiting evolution of molecular hydrogen.

47. The chemical reactor of claim 46 wherein the hydrogen formation catalyst is chosen from the group consisting of cadmium, lead, indium and mixtures thereof.

48. The chemical reactor of claim 19 wherein the mobile atom generation compartment side of the membrane comprises a hydride formation catalyst.

49. The chemical reactor of claim 48 wherein the hydride formation catalyst is chosen from the group consisting of palladium, titanium, vanadium, nickel, lanthanum and alloys, compounds and mixtures thereof.

* * * * *